US00PP17675P2

(12) United States Plant Patent
Takeshita et al.

(10) Patent No.: US PP17,675 P2
(45) Date of Patent: May 1, 2007

(54) ***PETUNIA* PLANT NAMED 'KIRIMAJI DOUBLE BLUE VELVET'**

(50) Latin Name: *Petunia×hybrida*
Varietal Denomination: Kirimaji Double Blue Velvet

(75) Inventors: Daigaku Takeshita, Tochigi-ken (JP); Saori Yamada, Tochigi-ken (JP)

(73) Assignee: Kirin Brewery Company, Ltd., Tokyo (JP)

( * ) Notice: Subject to any disclaimer, the term of this patent is extended or adjusted under 35 U.S.C. 154(b) by 27 days.

(21) Appl. No.: 11/284,044

(22) Filed: Nov. 21, 2005

(51) Int. Cl.
*A01H 5/00* (2006.01)

(52) U.S. Cl. ..... Plt./356

(58) Field of Classification Search ..... Plt./356
See application file for complete search history.

*Primary Examiner*—Kent Bell
*Assistant Examiner*—Annette H Para
(74) *Attorney, Agent, or Firm*—Audrey Charles

(57) ABSTRACT

A new and distinct cultivar of *Petunia* plant named 'Kirimaji Double Blue Velvet', characterized by its double-type, dark violet-colored flowers, medium green-colored foliage, excellent branching characteristics, and vigorous, low mounded and cascading growth habit.

1 Drawing Sheet

Latin name of genus and species of plant claimed: *Petunia×hybrida.*
Variety denomination: 'Kirimaji Double Blue Velvet'.

BACKGROUND OF THE INVENTION

The present invention relates to a new and distinct cultivar of *Petunia* plant botanically known as *Petunia×hybrida* and hereinafter referred to by the cultivar name 'Kirimaji Double Blue Velvet'.

The new cultivar originated in a controlled breeding program in Tochigi, Japan during March 2003. The objective of the breeding program was the development of new double-type *Petunia* cultivars have a strong, spreading growth habit and attractive flower coloration.

The female (seed) parent of the new cultivar was the unnamed proprietary *Petunia×hybrida* breeding selection, not patented, characterized by its single-type, dark purple-colored flowers, dark green-colored foliage, and low mounded, cascading growth habit. The male (pollen) parent of the new cultivar was 'Petudre Violet', not patented, characterized by its semi-double type, violet-colored flowers, medium green-colored foliage, and medium mounded, cascading growth habit. The new *Petunia* was discovered and selected as a single flowering plant within the progeny of the above stated cross-pollination during October 2003 in a controlled environment at Tochigi, Japan.

Asexual reproduction of the new cultivar by terminal stem cuttings since October 2003 at Tochigi, Japan and West Chicago, Ill. has demonstrated that the new cultivar reproduces true to type with all characteristics, as herein described, firmly fixed and retained through successive generations of such asexual propagation.

SUMMARY OF THE INVENTION

The following characteristics of the new cultivar have been repeatedly observed and can be used to distinguish 'Kirimaji Double Blue Velvet' as a new and distinct cultivar of *Petunia* plant:

1. Double-type, dark violet-colored flowers;
2. Medium green-colored foliage;
3. Excellent branching characteristic; and
4. Vigorous, low mounded, and cascading growth habit.

Plants of the new cultivar differ from plants of the female parent primarily in flower type and foliage color and from plants of the male parent primarily in flower type and growth habit.

Of the many commercially available *Petunia* cultivars known to the inventors, the most similar in comparison to the new cultivars is 'Kirimaji Double Purple', U.S. Plant Pat. No. 14,283. However, in side by side comparisons, plants of the new cultivar differ from plants of 'Kirimaji Double Purple' in the following characteristics:

1. Plants of the new cultivar are shorter and wider than plants of 'Kirimaji Double Purple';
2. Plants of the new cultivar have more and larger flowers than plants of 'Kirimaji Double Purple';
3. Plants of the new cultivar have more branches than plants of 'Kirimaji Double Purple'; and
4. Plants of the new cultivar have a different flower color from plants of 'Kirimaji Double Purple'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Kirimaji Double Blue Velvet'. The plants were grown in 10 cm pots for 11 weeks in a greenhouse at West Chicago, Ill.

DETAILED BOTANICAL DESCRIPTION

Figure 1:
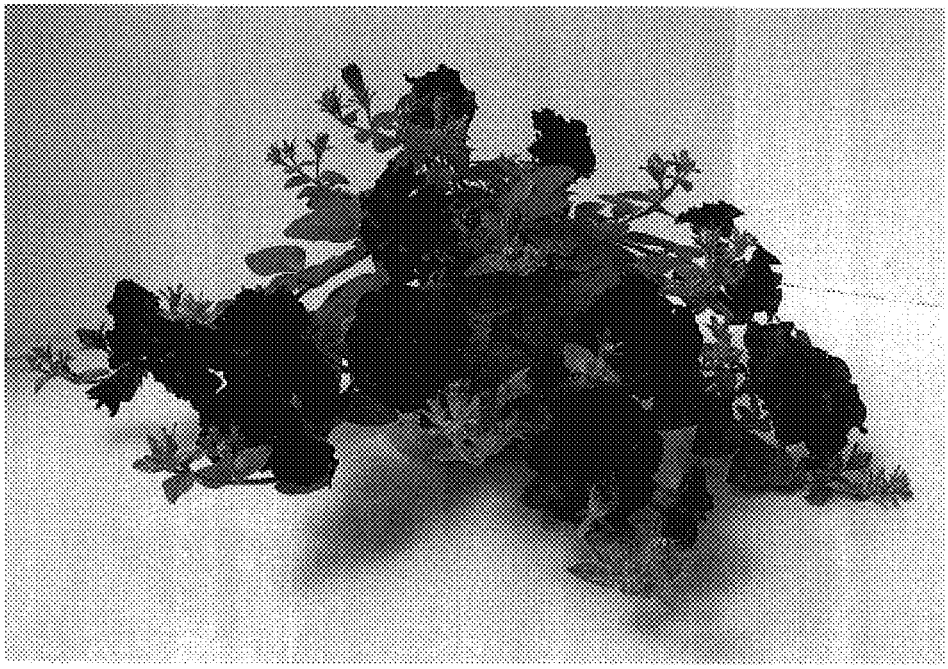
FIG. 1 illustrates a side view of the overall growth and flowering habit of 'Kirimaji Double Blue Velvet'.
Figure 2:
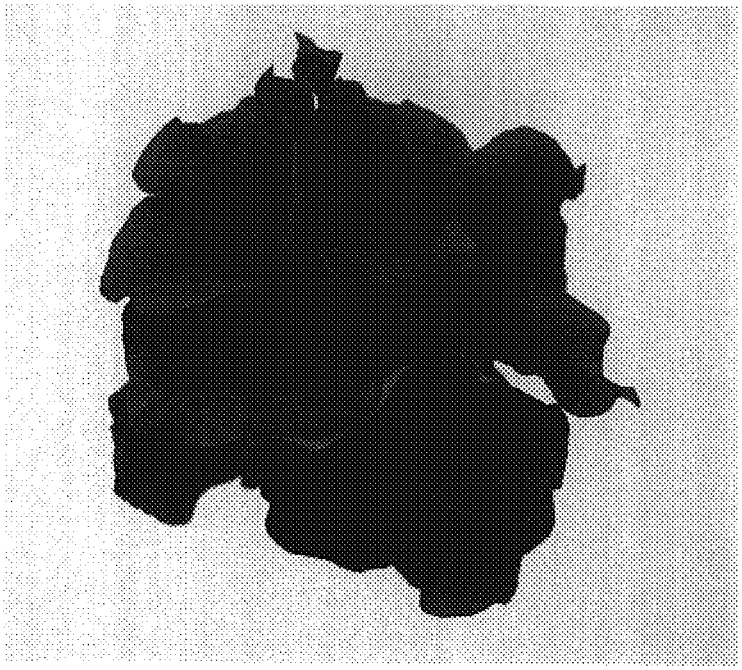
FIG. 2 illustrates a close-up view of an individual flower of 'Kirimaji Double Blue Velvet'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Sep. 6, 2005 between 3:00 p.m. and 4:00 p.m. under natural light conditions, in West Chicago, Ill.

The following descriptions and measurements describe plants produced from cuttings taken from stock plants and grown in a double polycarbonate-covered greenhouse under conditions comparable to those used in commercial practice. The plants were grown at West Chicago, Ill. in 10 cm pots for 11 weeks utilizing a soilless growth medium. Greenhouse temperatures were maintained at approximately 58° F. to 75° F. (14° C. to 24° C. during the day and approximately 52° F. to 62° F. (11° C. to 17° C.) during the night. Greenhouse light levels of 5,000 to 8,000 footcandles were maintained during the day.

Botanical classification: *Petunia×hybrida* cultivar Kirimaji Double Blue Velvet.

Parentage:

*Female parent.*—Unnamed proprietary *Petunia×hybrida* breeding selection, not patented.

*Male parent.*—'Petudre Violet', not patented.

Propagation:

*Type cutting.*—Terminal stem.

*Time to initiate roots.*—Approximately 6 to 9 days.

*Time to produce a rooted cutting.*—Approximately 21 to 28 days.

*Root description.*—Fibrous.

*Rooting habit.*—Freely branching.

Plant description:

*Crop time.*—Approximately 6 to 8 weeks from a rooted cutting.

*Growth habit and general appearance.*—Vigorous, low mounded, cascading.

*Size.*—Height from soil level to top of plant plane: Approximately 10.8 cm. Width: Approximately 55.5 cm.

*Branching habit.*—Freely basal branching. Approximately 4 main branches per plant with lateral branches forming at every node.

*Branch.*—Strength: Strong. Length: Approximately 33.1 cm. Diameter: Approximately 3.1 mm. Texture: Densely pubescent with a mixture of long hairs and short glandular hairs. Color of mature stem: 144A. Internode length at center of branch: Approximately 2.6 cm.

*Foliage.*—Number of leaves per main branch: Approximately 19. Fragrance: None. Form: Simple. Arrangement on flowering stem: Alternate. Aspect: At right angle to stem. Shape: Ovate. Margin: Entire. Apex: Acute. Base: Attenuate. Venation pattern: Pinnate. Length of mature leaf: Approximately 5.6 cm. Width of mature leaf: Approximately 3.7 cm. Texture of upper and lower surfaces: Densely pubescent. Color of upper surface of mature foliage: 146A with venation of 146D. Color of lower surface of mature foliage: 146B with venation of 146D. Petiole length: Approximately 7.0 mm. Petiole diameter: Approximately 2.3 mm. Petiole texture: Densely pubescent. Petiole color: 145B.

Flowering description:

*Flowering habit.*—'Kirimaji Double Blue Velvet' is freely flowering under outdoor growing conditions with substantially continuous blooming from spring through autumn and year round in greenhouse environment.

*Time to first flower.*—Approximately 11 weeks after sticking of unrooted cutting.

*Lastingness of individual bloom.*—Approximately 5 to 7 days.

Flower description:

*Type.*—Double, solitary, funnelform. Quantity per plant at eleven weeks: Approximately 13.

*Bud rate of opening.*—Generally takes 1 to 2 days for bud to progress from first color to fully open flower.

*Bud just before opening.*—Quantity per plant at 11 weeks: 12. Shape: Elongated, globular. Length: Approximately 3.1 cm. Diameter at apex: Approximately 1.9 cm. Diameter at base: Approximately 5.0 mm. Texture: Densely pubescent. Color: 86C.

*Corolla.*—Diameter: Approximately 7.4 cm. Depth: Approximately 2.5 cm.

*Petals.*—Quantity: Approximately 23, fused for most of their length. Shape: Obovate. Apex: Sharply acute. Margin: Entire. Appearance: Velvety. Texture of upper surface: Glabrous. Texture of lower surface: Moderately pubescent with dense pubescence along veins. Petal length from tube: Approximately 2.5 cm. Petal length of free portion: 1.4 cm. Petal width: Approximately 2.4 cm. Color of upper surface when fully open: Between 86A and N88A with venation of 79A. Color of lower surface when fully open: 86B with midvein of 149D.

*Corolla tube.*—Length: Approximately 2.6 cm. Diameter at distal end: Approximately 2.4 cm. Diameter at proximal end: Approximately 5.1 mm. Texture of inner surface: Glabrous. Texture of outer surface: Lanate. Color inner surface: N81A with venation of N186B. Color outer surface: N88D with venation of 145A.

*Peduncle.*—Strength: Strong. Aspect: Acute angle to stem. Length: Approximately 3.1 cm. Diameter: Approximately 1.9 mm. Texture: Densely glandular pubescent. Color: 144A.

*Sepals.*—Quantity per flower: 5 fused at base. Shape: Linear. Apex: Obtuse. Sepal length: Approximately 1.4 cm. Sepal width: Approximately 2.6 mm. Texture of upper and lower surfaces: Densely pubescent. Color of upper surface: 146A. Color of lower surface: 146B.

*Reproductive organs.*—Androecium: Stamen quantity: Approximately 12. Stamen length: Approximately 3.0 cm. Filament color: 157A. Anther shape: Bilobed. Anther length: Approximately 1.0 mm. Anther color: Closest to N92C. Pollen amount: None observed. Gynoecium: Pistil quantity: One per flower. Pistil length: Approximately 5.0 mm. Stigma shape: Funnel. Stigma length: Approximately 1.0 mm. Stigma color: 146B. Style length: Approximately 1.0 mm. Style color: 145B. Ovary diameter: Approximately 3.0 mm. Ovary color: 145A.

Seed and fruit production: Neither seed nor fruit production has been observed.

Disease and pest resistance: Resistance to pathogens and pests common to *Petunia* has not been observed.

What is claimed is:

1. A new and distinct cultivar of *Petunia* plant named 'Kirimaji Double Blue Velvet', substantially as herein shown and described.

* * * * *